(12) United States Patent
Sadiq et al.

(10) Patent No.: US 7,790,402 B2
(45) Date of Patent: Sep. 7, 2010

(54) FETUIN-A AS A BIOMARKER FOR MULTIPLE SCLEROSIS

(75) Inventors: Saud Ahmed Sadiq, Franklin Lakes, NJ (US); Nicola Renee Donelan, New York, NY (US); Qi Jiang Yan, Forest Hills, NY (US)

(73) Assignee: Multiple Sclerosis Research Center of New York, New York, NY (US)

( * ) Notice: Subject to any disclaimer, the term of this patent is extended or adjusted under 35 U.S.C. 154(b) by 97 days.

(21) Appl. No.: 11/856,454

(22) Filed: Sep. 17, 2007

(65) Prior Publication Data
US 2008/0268479 A1    Oct. 30, 2008

Related U.S. Application Data

(60) Provisional application No. 60/845,390, filed on Sep. 18, 2006, provisional application No. 60/856,559, filed on Nov. 3, 2006.

(51) Int. Cl.
*G01N 33/53* (2006.01)
(52) U.S. Cl. ...................................... 435/7.1
(58) Field of Classification Search .................. None
See application file for complete search history.

(56) References Cited

U.S. PATENT DOCUMENTS

2005/0260678 A1 * 11/2005 Tomosugi et al. ............ 435/7.1

FOREIGN PATENT DOCUMENTS

WO    2007/041245    *    4/2007

OTHER PUBLICATIONS

Dumont 2004 (Proteomics 4:2117-2124).*
Fagnart, O.C., et al., "Particle-Counting Immunoassay of a Fetuin-Like Antigen in Serum and Cerebrospinal Fluid" Clinical Chemistry 31(11):1820-1823 (1985).
Donelan, N.R., et al., "Fetuin-A Levels are Elevated in Cerebospinal Fluid of Patients with Secondary Progressive Multiple Sclerosis" Neurology 66(5) Supplement 2:A371 (Mar. 2006).
Miller, D.H., et al.; "A Controlled Trial of Natalizumab for Relapsing Multiple Sclerosis" New England Journal of Medicine 348:15-23 (2003).
Sadiq, S.A., et al.; "Cerebrospinal Fluid Proteomic Analysis Reveals Altered Protein Profiles in Multiple Sclerosis" Neurology 66(5) Supplement 2:A175 (Mar. 2006).
Sospedra, M. and Martin, R., Immunology of multiple sclerosis. Annu Rev Immunol 23. 683 (2005).
(Katz, D. et al., Correlation between magnetic resonance imaging findings and lesion development in chronic, active multiple sclerosis. Ann Neurol 34 (5), 661 (1993)).
(Triffitt, J.T. et al., Origin of Plasma alpha2HS-glycoprotein and its accumulation in bone. Nature 262 (5565), 226 (1976)).
(Dziegielewska, K. et al., The expression of fetuin in the development and maturation of the hemopoietic and immune system. Histochem Cell Biol 106 (3), 319 (1996)).

(Kellermann, J., Haupt, H., Auerswald, E., A., and Muller-Ester, W., The arrangement of disulfide loops in human alpha 2-HS glycoprotein . . . J. Biol Chem 264 (24), 14121 (1989)).
(Szweras, M., et al ., alpha 2HS glycoprotein/fetuin, a transforming growth factor-beta /bone morphogenetic protein antagonist, regulates1 . . . J. Biol Chem 277 (22), 1991(2002)).
(Mathews, S.T. et al., Improved insulin sensitivity and resistance to weight gain in mice null for the Ahsg gene. Diabetes 51 (8), 2450 (2002)).
(Heiss, A. et al., Structural basis of calcification inhibition by alpha 2-HS glycoprotein/fetuin-A. Formation of colloidal calciprotein . . . J Biol Chem 278 (15), 1333 (2003).
Schafer, C. et al., The serum protein alpha 2-Heremans-Schmid glycoprotein/fetuin-A is a systematically acting inhibitor of ectopic . . . J Clin Invest 112 (3), 357 (2003).
Schinke, T. et al., The serum protein alpha -HS glycoprotein/fetuin inhibits apatite formation in vitro and in mineralization calvaria . . . J Biol Chem 271 (34), 20789 (1996).
(Jahnen-Dechent, W. et al., Cloning and targeted deletion of the mouse fetuin gene. J Biol Chem 272 (50), 31496 (1997).
(Kundranda, M.N. et al., Annexins expressed on the cell surface serve as receptors for ashesion to immobilized fetuin-A. Biochim Biophys Acta 1693 (2), 111 (2004)).
(Lebreton, J.P. et al., Serum concentration of human alpha 2 HS glycoprotein during the inflammatory process; evidence that alpha 2 HS . . . J Shin Invest 64 (4), 1118 (1979)).
(Dziegielewska, K.M., Andersen, N.A. and Saunders, N.R., Modification of macrophage resopnse to lipopolusaccharide by fetuin. Immunol Lett 60 (1), 31 (1998)).
(Ombrellino, M. et al. Fretuin, a negative acute phase protein, attenuates TNF synthesis and the innate inflammatory response to carrageenan Shock 15 (3), 181 (2001)).
(Demetriou, M. et al., Fetuin/alpha2-HS glycoprotein is a transforming growth factorbeta type II receptor mimic and cytokine antagonist. J Biol Chem 271 (22), 12755 (1996)).
(Carrieri, P.B. et al., Possible role of transforming growth factor-beta in relapsing-remitting multiple sclerisis. Neurol Res 19 (6). 599 (1997)).
(Moustakas, A., Pardali, J., Gaal, A., and Heldin, C.H. Mechanisms of TGF-beta signaling in regulation of cell growth and differentiation, Immunol Lett 82 (1-2), 85 (2002)).
Letterio, J., J. and Roberts, A.B., Regulation of immune response by TGF-beta. Annu Rev Immunol 16, 137 (1998)).
(Leppert, D. et al., T cell gelatinases mediate basement membrane transmigration in vitro. J. Immunol 154 (9), 4379 (1995).
Stuve, O. et al., Interferon beta-1b decreases the migration of T lymphocytes in vitro: effects on matrix metalloproteinase-9 . Ann Neurol 40 (6),853 (1996).
Lukes, A., Mun-Bryce, S., Lukes , M., and Rosenberg, G.A., Extracellular matrix degradation by metalloproteinases and central nervous . . . Mol Neurobiol 19 (3), 267 (1999)).

(Continued)

*Primary Examiner*—Daniel E. Kolker
(74) *Attorney, Agent, or Firm*—Scully, Scott, Murphy & Presser, P.C.

(57) ABSTRACT

Biomarkers are disclosed that facilitate the mechanisms associated with central nervous system disease worsening or activity, specifically multiple sclerosis. Methods are also disclosed for identification of biomarkers associated with disease worsening or activity in multiple sclerosis.

3 Claims, 16 Drawing Sheets

OTHER PUBLICATIONS (Ochieng J. and Green, B., The interactions of alpha 2 HS glycoprotein with metalloproteinases. Biochem Mol Biol Int 40 (1), 13 (1996)).

(Tajirian, T., Dennis, J.W., and Swallow, C.J.., Regulation of human monocyte proMMP-9 production by fetuin, an endogenous TGF-beta . . . J Cell Physiol 185 (2), 174 (2000)).

(Srinivas, P.R., Kramer, B.S., and Srivastava, S., Trends in biomarker research for cancer detection. Lancet Oncol 2 (11), 698 (2001)).

(Sorensen, T. L. et al., Chemokines CXCL10 and CCL2; differential involvement in intrathecal inflammation in multiple sclerosis. Eur J Neurol 8 (6), 665 (2001)).

(Rosenberg, G.A., Matrix metalloproteinases biomarkers in multiple sclerosi. Lancet 365 (9467), 1291 (2005)).

Stromnes, I. M. and Goverman, J.M., Active induction of experimental allergic encephalomyelitis. Nat Protoc 1 (4), 1810 (2006).

Lehmensick et al., Cerebrospinal fluid proteome profile in Multiple Sclerosis, Multiple Sclerosis 2007;13: 840-849.

Virley, D.J., "Developing Therapeutics for the Treatment of Multiple Sclerosis" *Journal of the American Society for Experimental Neuro Therapeutics* (2005) pp. 638-649, vol. 2(4).

Bielekova, B. et al., "Development of Biomarkers in Multiple Sclerosis" *Brain* (2004) pp. 1463-1478, vol. 127(7).

Extended European Search Report dated Feb. 16, 2010.

* cited by examiner

| Control | | | PPMS | | | SPMS | | |
|---|---|---|---|---|---|---|---|---|
| Patient ID | Peak Intensity | Sex/Age | Patient ID | Peak Intensity | Sex/Age | Patient ID | Peak Intensity | Sex/Age |
| MC002-1* | 0.0504 | F/26 | VS030-1* | 0.0834 | F/50 | SM007-2* | 0.0823 | M/58 |
| LC009-1* | 0.0392 | F/34 | NS032-1* | 0.0709 | M/39 | FS023-1* | 0.1332 | F/59 |
| DT011-1* | 0.0435 | F/48 | BP035-1* | 0.0315 | F/38 | BS022-1* | 0.1384 | M/52 |
| WC015-1* | 0.0447 | M/24 | LW038-1* | 0.061 | F/53 | ML026-1* | 0.0513 | F/51 |
| LP016-1* | 0.0717 | F/46 | SP058-1* | 0.0868 | M/42 | DD025-1* | 0.0591 | F/49 |
| JG019-1* | 0.0293 | F/58 | LP067-1* | 0.0602 | F/60 | JR065-1* | 0.092 | M/55 |
| HW028-1* | 0.0745 | M/62 | SM004-2* | 0.0657 | F/44 | AK084-1* | 0.1035 | M/47 |
| JM085-1* | 0.0662 | M/26 | DR010-1* | 0.0556 | F/48 | TT006-2* | 0.0689 | F/41 |
| DT011-2* | 0.0564 | F/48 | MA012-2* | 0.0472 | M/46 | RW014-2* | 0.0669 | F/47 |
| LP016-2* | 0.0692 | F/46 | HY008-2* | 0.0482 | M/72 | KW017-3* | 0.0641 | M/29 |
| MB061-1 | 0.0716 | M/54 | JM043-1 | 0.0879 | M/71 | JC034-1 | 0.0965 | F/38 |
| AT076-1 | 0.0428 | F/36 | RK047-1 | 0.0705 | M/67 | SC060-1 | 0.1072 | M/42 |
| EM105-1 | 0.0822 | M/68 | HW051-1 | 0.0593 | M/52 | PW066-1 | 0.1011 | F/64 |
| | | | NB056-1 | 0.0796 | M/51 | MC070-1 | 0.1181 | F/30 |
| | | | LS075-1 | 0.0909 | F/61 | DM071-1 | 0.0435 | F/39 |
| | | | AM074-1 | 0.0741 | F/38 | BW072-1 | 0.138 | M/40 |
| | | | RT083-1 | 0.0912 | M/50 | MG073-1 | 0.1118 | F/56 |
| | | | JS086-1 | 0.1144 | M/35 | JM077-1 | 0.077 | F/50 |
| | | | JM091-1 | 0.0566 | M/44 | ED081-1 | 0.1417 | F/57 |
| | | | JB099-1 | 0.0717 | F/53 | DS098-1 | 0.0555 | F/45 |
| Median | 0.0564 | | Median | 0.0707 | | Median | 0.0943 | |

Figure 3

| Kruskal-Wallis test p-value | | |
|---|---|---|
| All Samples | Pump samples | Non-Pump samples |
| 0.0031 | 0.0387 | 0.1090 |
| Post-hoc Mann-Whitney test (All samples) | | |
| CON vs PP | CON vs SP | PP vs SP |
| 0.0554 | 0.0022 | 0.0326 |
| Receiver Operator Characteristic AUC (All samples) | | |
| CON vs PP | CON vs SP | PP vs SP |
| 0.6375 | 0.7875 | 0.6900 |

Figure 4

```
  1           11          21          31          41          51
  1 MKSLVLLLCL AQLWGCHSAP HGPSLIYRQP NCDDPETERA ALVAIDYINQ NLPWGYKHTL   60
 61 NQIDEVKVWP QQPSGELFEI EIDTLETTCH VLDPTPVARC SVRQLKEHAV EGDCDFQLLK  120
121 LDGKFSVVYA KCDSSPDSAE DVRKVCQDCP LLAPLNDIRV VHAAKPALAA FNAQMNGSNF  180
181 QLEEISRAQL VPLPPSTYVE FTVSGTDCVA KRATEAAKCN LLAEKQYGFC KATLSEKLGG  240
241 AHVAVTCTVF QTQPVTSQPQ PEGANEAVPT PVVDEDAPPS PPIGAPGLPP AGSPPDSHVL  300
301 LAAPPGHQLH RAHYDLRHTF MGVVSLGSPS GEVSHPRKTR TVVQPSVGAA AGPVVPPCPG  360
361 RIRHPKV
```

(SEQ ID NO:1)

Figure 5

SEQUENCE LISTING

```
<160> NUMBER OF SEQ ID NOS: 6

<210> SEQ ID NO 1
<211> LENGTH: 367
<212> TYPE: PRT
<213> ORGANISM: Homo sapiens

<400> SEQUENCE: 1

Met Lys Ser Leu Val Leu Leu Leu Cys Leu Ala Gln Leu Trp Gly Cys
 1               5                  10                  15

His Ser Ala Pro His Gly Pro Gly Leu Ile Tyr Arg Gln Pro Asn Cys
             20                  25                  30

Asp Asp Pro Glu Thr Glu Glu Ala Ala Leu Val Ala Ile Asp Tyr Ile
         35                  40                  45

Asn Gln Asn Leu Pro Trp Gly Tyr Lys His Thr Leu Asn Gln Ile Asp
     50                  55                  60

Glu Val Lys Val Trp Pro Gln Gln Pro Ser Gly Glu Leu Phe Glu Ile
 65                  70                  75                  80

Glu Ile Asp Thr Leu Glu Thr Thr Cys His Val Leu Asp Pro Thr Pro
                 85                  90                  95

Val Ala Arg Cys Ser Val Arg Gln Leu Lys Glu His Ala Val Glu Gly
            100                 105                 110

Asp Cys Asp Phe Gln Leu Leu Lys Leu Asp Gly Lys Phe Ser Val Val
        115                 120                 125

Tyr Ala Lys Cys Asp Ser Ser Pro Asp Ser Ala Glu Asp Val Arg Lys
    130                 135                 140

Val Cys Gln Asp Cys Pro Leu Leu Ala Pro Leu Asn Asp Thr Arg Val
145                 150                 155                 160

Val His Ala Ala Lys Ala Ala Leu Ala Ala Phe Asn Ala Gln Asn Asn
                165                 170                 175

Gly Ser Asn Phe Gln Leu Glu Glu Ile Ser Arg Ala Gln Leu Val Pro
            180                 185                 190

Leu Pro Pro Ser Thr Tyr Val Glu Phe Thr Val Ser Gly Thr Asp Cys
```

-continued

```
                195                 200                 205

Val Ala Lys Glu Ala Thr Glu Ala Ala Lys Cys Asn Leu Leu Ala Glu
    210                 215                 220

Lys Gln Tyr Gly Phe Cys Lys Ala Thr Leu Ser Glu Lys Leu Gly Gly
225                 230                 235                 240

Ala Glu Val Ala Val Thr Cys Thr Val Phe Gln Thr Gln Pro Val Thr
                245                 250                 255

Ser Gln Pro Gln Pro Glu Gly Ala Asn Glu Ala Val Pro Thr Pro Val
            260                 265                 270

Val Asp Pro Asp Ala Pro Pro Ser Pro Pro Leu Gly Ala Pro Gly Leu
    275                 280                 285

Pro Pro Ala Gly Ser Pro Pro Asp Ser His Val Leu Leu Ala Ala Pro
290                 295                 300

Pro Gly His Gln Leu His Arg Ala His Tyr Asp Leu Arg His Thr Phe
305                 310                 315                 320

Met Gly Val Val Ser Leu Gly Ser Pro Ser Gly Glu Val Ser His Pro
                325                 330                 335

Arg Lys Thr Arg Thr Val Val Gln Pro Ser Val Gly Ala Ala Ala Gly
            340                 345                 350

Pro Val Val Pro Pro Cys Pro Gly Arg Ile Arg His Phe Lys Val
        355                 360                 365

<210> SEQ ID NO 2
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 2
ctcagccgag gacgtgcgca agg                                              23

<210> SEQ ID NO 3
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 3
tgagcccggg aaatttcctc c                                                21

<210> SEQ ID NO 4
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 4
atcccatcac catcttccag                                                  20

<210> SEQ ID NO 5
<211> LENGTH: 20
<212> TYPE: DNA
<213> ORGANISM: Artificial Sequence
<220> FEATURE:
<223> OTHER INFORMATION: Description of Artificial Sequence: Synthetic
      primer
```

```
<400> SEQUENCE: 5
tgagtccttc cacgatacca                                                      20

<210> SEQ ID NO 6
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 6

Met Glu Val Gly Trp Tyr Arg Pro Pro Phe Ser Arg Val Val His Leu
 1               5                  10                  15

Tyr Arg Asn Gly Lys
             20
```

FETUIN-A AS A BIOMARKER FOR MULTIPLE SCLEROSIS

CROSS REFERENCE TO RELATED APPLICATIONS

This application claims the benefit of U.S. Provisional Patent Application Ser. Nos. 60/845,390, filed Sep. 18, 2006 and 60/856,559, filed Nov. 3, 2006, both of which are incorporated by reference in their entirety.

FIELD OF THE INVENTION

The invention relates generally to the identification of biomarkers associated with disease worsening or activity in multiple sclerosis.

BACKGROUND OF THE INVENTION

Multiple Sclerosis

Multiple sclerosis (MS) is a chronic inflammatory disease of the central nervous system (CNS) and is second only to trauma as the major cause of acquired disability in young adult Caucasian populations. The disease usually starts between 20 to 40 years of age and there are two major forms. Relapsing-remitting MS (RR-MS) is the most frequent form (85%-90%) and affects women about twice as often as men. Most RR-MS patients later develop the second major form known as secondary progressive MS (SP-MS). About 10%-15% of patients show a steady progression following disease onset with the absence of relapses, termed primary progressive PP-MS. (Sospedra, M. and Martin, R. Immunology of multiple sclerosis. *Annu Rev Immunol* 23, 683 (2005)). MS is a highly heterogeneous disease where every patient differs in clinical presentation and response to treatments.

Disease activity in MS can be defined by a number of different parameters such as changes in number of gadolinium enhancing lesions (Katz, D. et al., Correlation between magnetic resonance imaging findings and lesion development in chronic, active multiple sclerosis. *Ann Neurol* 34 (5), 661 (1993)), Expanded Disability Status Scale (EDSS) scores and relapse rate. Gadolinium enhancing lesions imaged by Magnetic Resonance Imaging (MRI) is one of the most reliable indications of active inflammation in MS (see, Katz, Id.). However the MRI only monitors structural damage occurring in the brain, while much of the disease activity may be occurring in the spinal cord. In addition, while the MRI gives a clear indication of damage occurring in the brain, a biomarker has the advantage in that it can provide quantitative and more accurate measurements of disease activity. The discovery of a biomarker such as Fetuin-A protein which can consistently be used to predict the level of disease activity could translate to faster and more accurate therapeutic decisions by physicians and healthcare providers.

Fetuin-A

Fetuin-A, also known as Alpha$_2$ HS-glycoprotein, is a major serum protein in mammals mainly of hepatic origin being 95% liver-derived (Triffitt, J. T. et al., Origin of plasma alpha2HS-glycoprotein and its accumulation in bone. *Nature* 262 (5565), 226 (1976)). Expression in other cell types such as cells of monocyte/macrophage lineage during development and in the adult bone marrow has also been described. (Dziegielewska, K. et al., The expression of fetuin in the development and maturation of the hemopoietic and immune systems. *Histochem Cell Biol* 106 (3), 319 (1996)). Fetuin-A is a member of a family of related glycoproteins that belong to the cystatin superfamily (Kellermann, J., Haupt. H., Auerswald, E. A., and Muller-Ester, W., The arrangement of disulfide loops in human alpha 2-HS glycoprotein. Similarity to the disulfide bridge structures of cystatins and kininogens. *J Biol Chem* 264 (24), 14121 (1989). It has a diverse range of biological functions including osteogenesis and bone resorption (Szweras, M. et al., alpha 2-HS glycoprotein/fetuin, a transforming growth factor-beta/bone morphogenetic protein antagonist, regulates postnatal bone growth and remodeling. *J Biol Chem* 277 (22), 19991 (2002)), regulation of insulin activity (Mathews, S. T. et al., Improved insulin sensitivity and resistance to weight gain in mice null for the Ahsg gene. *Diabetes* 51 (8), 2450 (2002)), and inhibition of unwanted mineralization (Heiss, A. et al., Structural basis of calcification inhibition by alpha 2-HS glycoprotein/fetuin-A. Formation of colloidal calciprotein particles. *J Biol Chem* 278 (15), 13333 (2003); Schafer, C. et al., The serum protein alpha 2-Heremans-Schmid glycoprotein/fetuin-A is a systemically acting inhibitor of ectopic calcification. *J Clin Invest* 112 (3), 357 (2003); Schinke, T. et al., The serum protein alpha2-HS glycoprotein/fetuin inhibits apatite formation in vitro and in mineralizing calvaria cells. A possible role in mineralization and calcium homeostasis. *J Biol Chem* 271 (34), 20789 (1996)).

Fetuin-A knockout mice are fertile and show no gross anatomical abnormalities. There is however compromised serum inhibition of apatite formation and some animals develop ectopic microcalcifications in soft tissues, corroborating a role for fetuin in serum calcium homeostasis (Jahnen-Dechent, W. et al., Cloning and targeted deletion of the mouse fetuin gene. *J Biol Chem* 272 (50), 31496 (1997)). Annexin II and VI are the putative cell surface receptors for fetuin-A and require the presence of calcium ions for binding (Kundranda, M. N. et al., Annexins expressed on the cell surface serve as receptors for adhesion to immobilized fetuin-A. *Biochim Biophys Acta* 1693 (2), 111 (2004)). Integrins have been implicated as possible fetuin-A receptors since addition of antibody against β1 integrin substantially reduced the adherence of tumor cells to immobilized Fetuin-A in the presence of magnesium ions. (see, Kundranda, Id.)

Of particular interest is the immune regulatory functions of fetuin-A. It is classified as a negative acute-phase protein since its concentration in serum is down-regulated during episodes of trauma and acute inflammation (Lebreton, J. P. et al. Serum concentration of human alpha 2 HS glycoprotein during the inflammatory process: evidence that alpha 2 HS glycoprotein is a negative acute-phase reactant. J Clin Invest 64 (4), 1118 (1979)). Fetuin has anti-inflammatory properties in that it attenuates TNF-α synthesis by LPS-stimulated macrophages (Dziegielewska, K. M., Andersen, N. A., and Saunders, N. R., Modification of macrophage response to lipopolysaccharide by fetuin. *Immunol Lett* 60 (1), 31 (1998)) and in an LPS-independent model of acute inflammation (Ombrellino, M. et al., Fetuin, a negative acute phase protein, attenuates TNF synthesis and the innate inflammatory response to carrageenan. Shock 15 (3), 181 (2001)).

Fetuin-A is also a TGF-β antagonist, and binds directly to TGF-β1 and TGF-β2. Fetuin-A blocks binding of TGF-β1 to the TGF-β receptor type 2 and therefore inhibits signaling through this major receptor. (Demetriou, M. et al., Fetuin/alpha2-HS glycoprotein is a transforming growth factor-beta type II receptor mimic and cytokine antagonist. *J Biol Chem* 271 (22), 12755 (1996)). Interestingly, a prior study showed that lower levels of TGF-β are present in the cerebrospinal fluid ("CSF") of MS patients during periods of disease activity when compared to periods of remission or inactivity (Carrieri, P. B. et al., Possible role of transforming growth factor-beta in relapsing-remitting multiple sclerosis. *Neurol Res* 19

(6), 599 (1997)). Since fetuin-A is an antagonist of TGF-β it is plausible that high levels of fetuin-A may affect levels and/or the activity of TGF-β. Reduced TGF-β activity could contribute to central nervous system ("CNS") inflammation since it is a potent immunosuppressor (Moustakas, A., Pardali, K., Gaal, A., and Heldin, C. H., Mechanisms of TGF-beta signaling in regulation of cell growth and differentiation. *Immunol Lett* 82 (1-2), 85 (2002) and suppresses the growth and differentiation of most immune cell lineages including B and T cells (Letterio, J. J. and Roberts, A. B., Regulation of immune responses by TGF-beta. *Annu Rev Immunol* 16, 137 (1998)).

MS pathology is characterized by blood brain barrier ("BBB") breakdown which leads to the infiltration of macrophages and lymphocytes into the CNS resulting in areas of demyelination or plaques. Matrix metalloproteinases ("MMPs") are a family of enzymes that degrade specific components of the extracellular matrix and have been implicated in the breakdown of and transmigration of immune cells across the BBB in MS (Leppert, D. et al., T cell gelatinases mediate basement membrane transmigration in vitro. *J Immunol* 154 (9), 4379 (1995); Stuve, O. et al., Interferon beta-1b decreases the migration of T lymphocytes in vitro: effects on matrix metalloproteinase-9. *Ann Neurol* 40 (6), 853 (1996); Lukes, A., Mun-Bryce, S., Lukes, M., and Rosenberg, G. A., Extracellular matrix degradation by metalloproteinases and central nervous system diseases. *Mol Neurobiol* 19 (3), 267 (1999)). Fetuin-A has been shown to associate with MMPs with the strongest association being with MMP-9 (Ochieng. J. and Green, B. The interactions of alpha 2HS glycoprotein with metalloproteinases. *Biochem Mol Biol Int* 40 (1), 13 (1996)). MMP-9 is produced by cells of the monocyte lineage and exists in an inactive form (proMMP-9) which is cleaved by proteinases to produce the active form. Fetuin-A was found to stimulate the release of pro-MMP-9 from a human monocytic cell line and from freshly isolated human peripheral blood monocytes, as well as activate proMMP-9 present in the THP-1 conditioned media (Tajirian, T., Dennis, J. W., and Swallow, C. J., Regulation of human monocyte proMMP-9 production by fetuin, an endogenous TGF-beta antagonist. *J Cell Physiol* 185 (2), 174 (2000)). It was shown that TGF-β1 has an inhibitory effect on the release of proMMP-9, and therefore fetuin-A being an antagonist of TGF-β1 can oppose this inhibitory effect on proMMP-9 release. This data suggests that under physiological conditions fetuin-A can contribute to matrix degradation.

Biomarkers

Biomarkers can be defined as biological molecules that are indicators of physiologic state and also of change during a disease process (Srinivas, P. R., Kramer, B. S., and Srivastava. S., Trends in biomarker research for cancer detection. *Lancet Oncol* 2 (11), 698 (2001)). A biomarker is only useful if it can be used to provide an early indication of the disease, if it can monitor disease progression, if it can be easily detected and if it can be a factor measurable across populations. The discovery of a reliable biomarker in MS is still an area of active research but the identification of reliable biomarkers can provide insight into the underlying mechanisms of disease progression and help to better predict the disease course. Over the years several groups have reported different proteins that they believed to be important biomarkers including the chemokines CXCL10, CCL2 (Sorensen, T. L. et al., Chemokines CXCL10 and CCL2: differential involvement in intrathecal inflammation in multiple sclerosis. *Eur J Neurol* 8 (6), 665 (2001)), and MMPs and tissue-inhibitors to metalloproteinases (TIMPs) (Rosenberg, G. A., Matrix metalloproteinases biomarkers in multiple sclerosis. *Lancet* 365 (9467), 1291 (2005)). One of the major challenges in biomarker discovery is obtaining an ample sample size and having uniformity in classification of patients. An ideal biomarker can be used for classification of MS patients, selecting the optimal course of treatment and for monitoring the response to those treatments.

SUMMARY OF THE INVENTION

Identifying biomarkers is particularly relevant to improving diagnosis, prognosis, and treatment of multiple sclerosis, and as such there is a need in the art for biomarkers that can be quickly, easily, and safely detected. The invention described herein utilizes a biomarker, Fetuin-A, to monitor the disease progression and the response to treatment of a subject with multiple sclerosis.

DESCRIPTION OF THE FIGURES

FIG. 3 illustrates the averaged intensity values for all samples for the 42.3 kDa peak detected on H50 Arrays;

FIG. 4 illustrates a summary of 42.3 kDa protein peak statistics;

FIG. 5 illustrates the amino acid sequence of the 42.3 kDa human Alpha 2-HS-Glycoprotein (Fetuin-A) (SEQ ID NO: 1);

DETAILED DESCRIPTION OF THE INVENTION

As used herein, the terms "polypeptide", "peptide" and "protein" (used interchangeably) refer to a polymer of amino acids. These terms do not connote a specific length of a polymer of amino acids. Thus, for example, the terms oligopeptide, protein, and enzyme are included within the definition of polypeptide or peptide, whether produced using recombinant techniques, chemical or enzymatic synthesis, or naturally occurring. This term also includes polypeptides that have been modified or derivatized, such as by glycosylation, acetylation, phosphorylation, and the like.

"Amino acid" is used herein to refer to a chemical compound with the general formula: $NH_2$—CRH—COOH, where R, the side chain, is H or an organic group. Where R is an organic group, R can vary and is either polar or nonpolar (i.e. hydrophobic).

Figure 1:
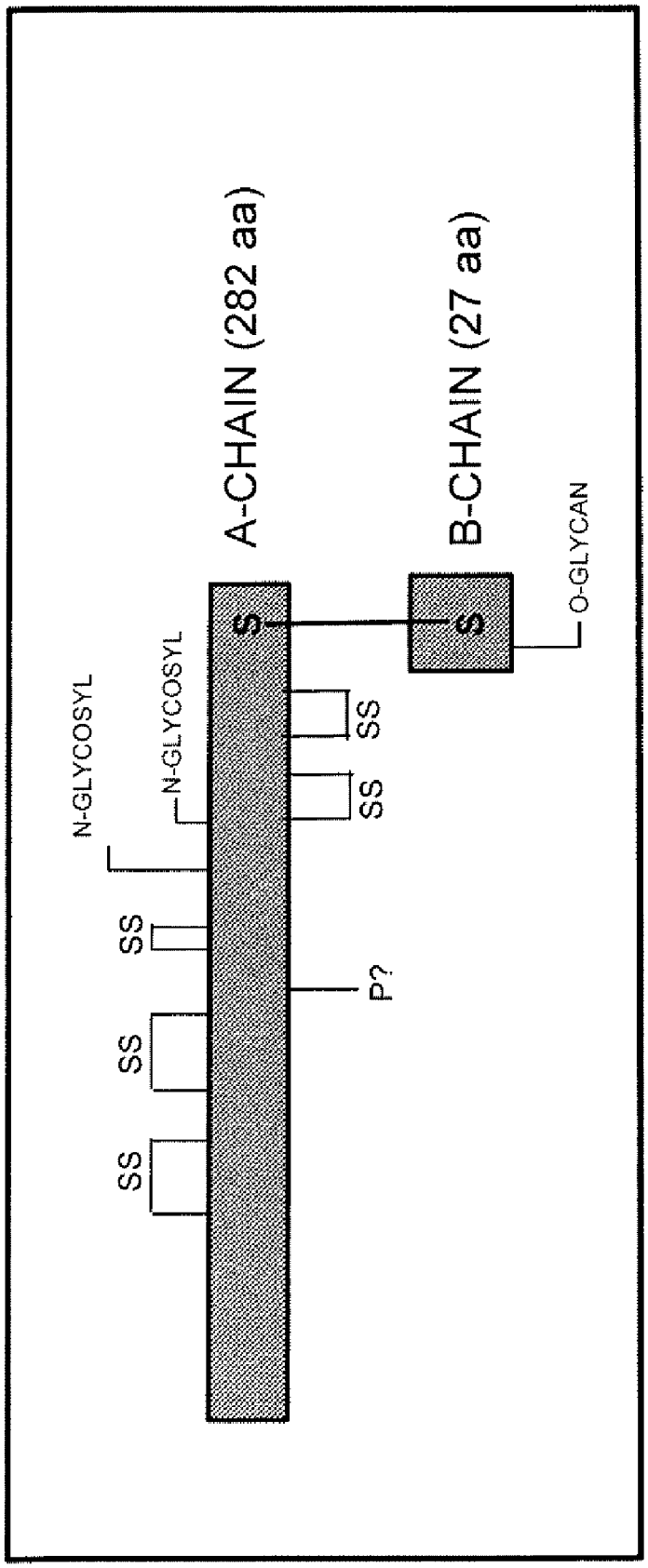
FIG. 1 is a schematic diagram of human Alpha 2-HS-glycoprotein (Fetuin-A)

A proteomics analysis of CSF from MS patients (PPMS and SPMS) and healthy controls was performed with the hope of finding novel protein biomarkers that were differentially regulated between the sample groups. Levels of a 42.3 kDa protein that was identified as Fetuin-A or Alpha$_2$ HS-glycoprotein were found to be significantly elevated in SPMS over PPMS and controls. A schematic diagram of the fetuin-A protein is shown in FIG. 1. Further investigation of the levels of Fetuin-A in the CSF of MS patients was done by ELISA (enzyme-linked immunosorbent assay) and that revealed a direct correlation between disease activity in MS and levels of Fetuin-A. Immunohistochemical analysis revealed that Fetuin-A could be found in various cell types of the CNS and that higher levels of Fetuin-A were found in regions of MS brains where there was a loss of myelin. The studies were extended to an animal model of MS (EAE) and similar localization of higher levels of Fetuin-A were found in areas of demyelination in the affected mouse spinal cord. Additionally, data shows that administration of Fetuin-A protein to mice with EAE causes worsening of the disease while administration of antibodies against Fetuin-A to these mice results in amelioration of EAE.

Those skilled in the art will appreciate that while ELISA and immunohistochemistry was used in the preceding procedures to measure protein levels, other biological assays such as, but not limited to, radioimmunoassay, protein chip assay, Western blot assay, microarray, fluoresence in situ hybridaztion (FISH), EITB (Electroimmunotransfer blot), FACTT (Fluorescent Amplification Catalyzed by T7 polymerase Technique), Nanotechnology (specifically using Biobarcodes), may be used to look at levels of proteins present in different biological sample. Furthermore, while CSF and autopsy brain tissue was tested as the biological sample, the invention is not intended to be limited in this respect and other biological samples may be tested, such as but not limited to, include plasma, serum, whole blood, urine, cerebrospinal fluid (CSF), lymph, sputum, saliva, tear fluid, tissue or cell lysates obtainable, for example, by biopsy, or by surgery, tissue culture supernatants, cell lysates obtained from in vitro cultured cells and organs.

Fetuin-A is a multifunctional protein with many activities that are involved in the regulation of immune responses and matrix metalloproteinase activity, however its presence in the CNS until now has not been linked to MS.

CSF Sample Selection for Proteomics Study

A total of fifty three CSF samples were analyzed. Samples were divided into three main groups; Controls (n-=3), PPMS (n=20), and SPMS (n=20). Samples were collected by two different methods either by side port aspiration from implanted pumps or by lumbar puncture.

Identification of Biomarkers

A SELDI-based (Surface Enhanced Laser Desorption Ionization) proteomics analysis was performed on CSF samples from the groups described above using Ciphergen Protein Chip® Array system. CSF samples were analyzed on a series of ProteinChip Arrays (CM10, H50, IMAC-Cu and Q10) under different binding conditions for a total of 14 different conditions. The data was analyzed using univariate and multivariate analysis to find a panel of candidate biomarkers.

The Kruskal-Wallis test was used to highlight peaks that showed a statistically significant difference between all three groups (Control, PPMS and SPMS). This test was used as a screening tool to identify candidate markers regardless of the mode of sample collection. Protein peaks that were highly significant (p-value less than 0.01) were visually inspected, manually relabeled, and further analyzed using the Kruskal-Wallis test for confirmation.

Following discovery of candidate markers, the Mann-Whitney test was used to characterize changes in protein peak intensity by comparing two groups at a time. The combinations tested were Control vs PPMS groups, Control vs SPMS groups and PPMS vs SPMS groups.

Finally, receiver operator characteristic (ROC) curves were plotted and the corresponding area under the curve (AUC) was calculated to assess their potential clinical utility. The ROC curve plots sensitivity versus 1-specificity. The area under the curve is indicative of the clinical utility of the marker to distinguish a patient group. All of the analysis was done using the Ciphergen Express Data Manager Software.

Figure 2:
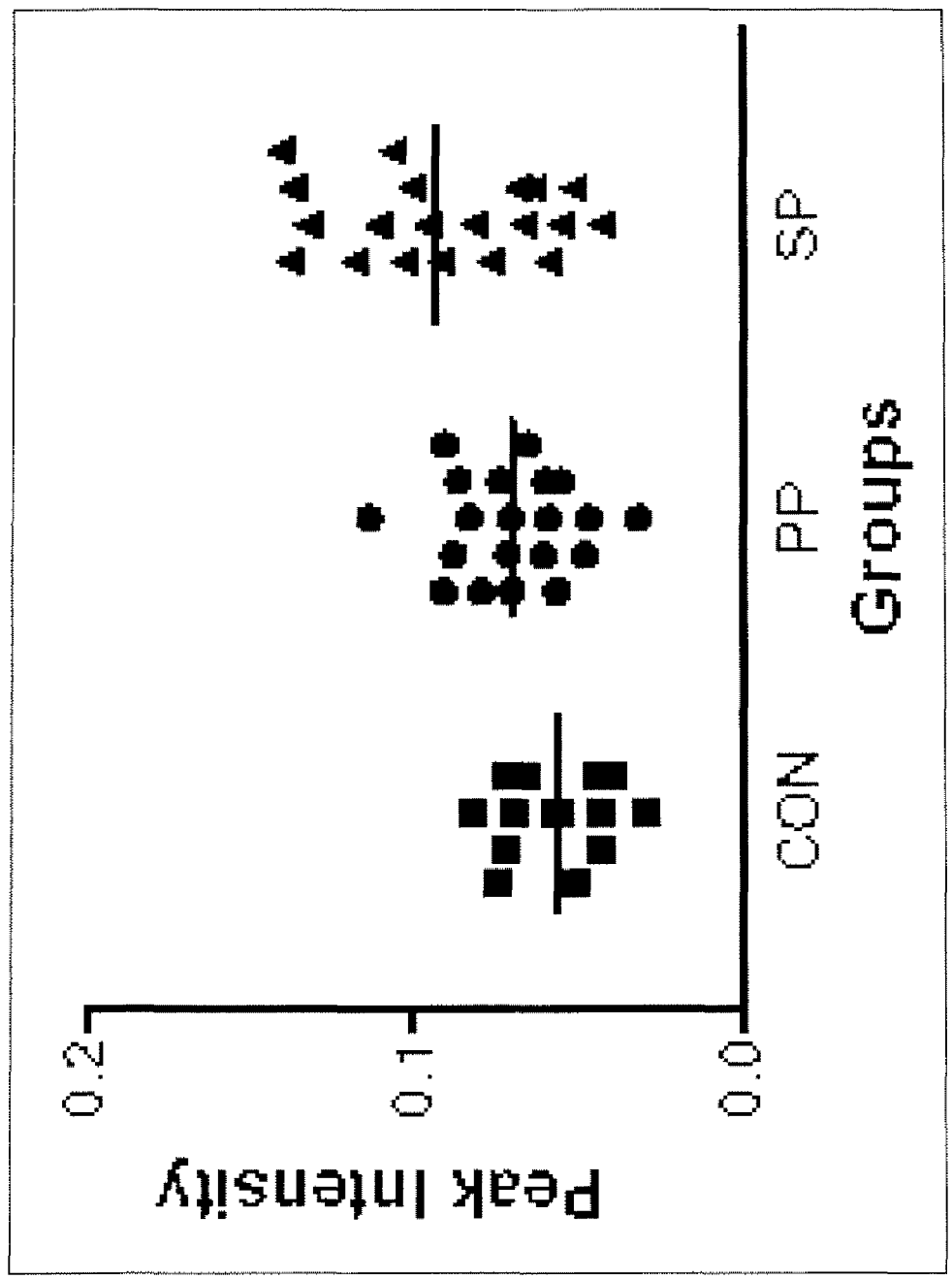
FIG. 2 is a scatter plot showing the peak intensities for the 42.3 kDa protein (Fetuin-A) within the three groups.

Levels of a protein peak of 42.3 kDa were found to have highly significant differences between the sample groups. A scatter plot shown in FIG. 2 illustrates the peak intensities for the 42.3 kDa protein (Fetuin-A) within the three groups. FIG. 3 shows the averaged intensity values for all samples for the 42.3 kDa peak detected on H50 Arrays. Analysis using the Mann-Whitney test showed that there was a significant increase in Fetuin-A levels in SPMS over controls (p=0.0022) and over PPMS (p=0.0326), and a summary of 42.3 kDa protein peak statistics are shown in FIG. 4.

Protein Identification and Sequencing

The protein of interest corresponding to the molecular mass of the detected peak was excised from a SDS-PAGE gel. The protein band was subjected to in-gel trypsin digestion. The peptides from the tryptic digest of the gel slice were detected on a tandem mass spectrometer equipped with a PCI-1000 ProteinChip Interface. The resulting patterns of ion fragments were submitted to the Mascot database search engine (Matrix Science, Boston, Mass.) for peptide sequence and protein identification.

A 42.3 kDa protein was detected on H50 arrays with 10% acetonitrile optimizing for the high mass range. Statistical analysis using the Kruskal-Wallis test revealed a significant difference in the peak intensities between the 3 groups (p=0.0031). The 42.3 kDa band was excised from a SDS-PAGE gel followed by in-gel trypsin digestion, protein mass fingerprinting and peptide sequencing identifying it as Fetuin-A or Alpha 2-HS-glycoprotein.

FIG. 5 illustrates the amino acid sequence of Fetuin-A in which peptide fragments with a single underline correspond to peptides detected after trypsin digestion of the 42.3 kDa gel band and used for CID tandem MS analysis for protein identification. The double underlined sequences of the peptides confirmed the identification of human Alpha 2-HS-Glycoprotein (Fetuin-A). The leader sequence of the protein (amino acids 1-18) is shown in italic letters. The identity of the band was confirmed by immunoprecipitating a 42.3 kDa protein from CSF with an anti-human Alpha 2-HS-Glycoprotein antibody.

Fetuin-A ELISA

Figure 6:
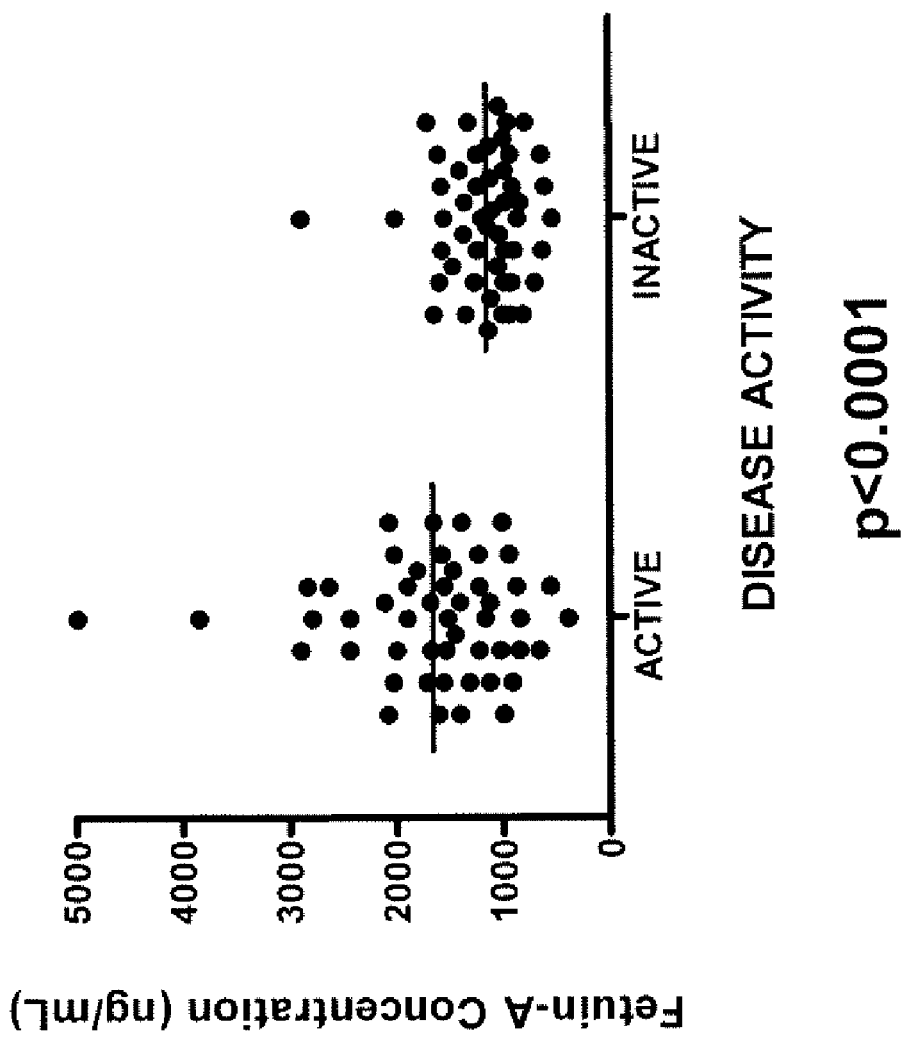
FIG. 6 graphically illustrates Fetuin-A concentration in cerebrospinal fluid vs. disease activity

Sterile procedure was used for obtaining CSF through lumbar puncture or from the side-port of a Medtronic pump. All samples were labeled with a code free of identifiers and aliquots of CSF were frozen at −70° C. Levels of Fetuin-A in the CSF were determined using the Fetuin ELISA kit from Biovendor (Cat.# RD19037100R), used according to the manufacturer's instructions. CSF Fetuin-A levels were analyzed by ELISA in 50 patients with active MS and 50 patients with inactive disease. Active disease in MS was defined by three parameters: (1) one or more relapses in the past 6 months; (2) change of one point or greater in EDSS (Expanded Disability Status Scale) score in the past 6 months; and (3) change in MRI, specifically a change in the number and/or size of lesions and the presence of gadolinium enhancing lesions in the past 6 months. CSF levels of Fetuin-A in patients with active disease was significantly elevated in comparison to patients with stable disease [mean 1655 ug/mL versus mean 1154 ug mL respectively, $p<0.0001$] as shown in FIG. 6.

Immunohistochemistry

In order to detect the presence and localization of proteins within cells immunohistochemical techniques were used. This technique uses primary monoclonal or polyclonal antibodies which are specific for a certain protein to "label" the protein of interest. Once the primary antibody is bound to its target protein a secondary antibody is used that binds to the primary antibody, the secondary antibody is then conjugated to a reporter enzyme (e.g., horseradish peroxidase) which allows for the visualization of the protein of interest.

Immunohistochemical staining was performed on frozen sections and paraffin-embedded tissue sections (5 μm) placed on ProbeOn Plus slides (Fisher Scientific). For paraffin sections, deparaffinized with xylene, and rehydrated through a series of graded alcohols. The endogenous alkaline phosphatase activity was blocked by 0.3% hydrogen peroxide. After microwave retrieval (H3300, Antigen unmasking solution for 10 minutes; Vector Laboratories, Inc., Burlingame, Calif., USA), the sections were blocked in 1×PBS/10% horse serum for 1 hour at room temperature and incubated with the first antibody for at least 16 hours at 4° C. A biotinylated secondary antibody coupled with streptavidin-horseradish peroxidase (Biotinylated secondary IgG+Vectastain ABC kit, Vector Laboratories, Inc.) was then used with 3,3-diaminobenzidine tetrahydrochloride (DAB) (Zymed. S. San Francisco, USA) as a substrate. The reaction between the peroxidase and the DAB produces a brown staining wherever primary and secondary antibodies are attached in a process known as DAB staining. Hematoxylin was used as the nuclear counterstain. The slides were mounted in Cytoseal 60 mounting medium (Richard-Allan Scientific) and examined by light microscopy. Polyclonal anti-human fetuin A/AHSG antibody (anti-Fetuin-A) was used at 1:500 dilution (AF 1184; R&D systems, Inc., USA and RD-910; Biovender laboratory Medicine, Inc., Czech Republic). Polyclonal anti-mouse fetuin A was used at 1:500 dilution (F-20; Santa Cruz Biotechnology Inc., Santa Cruz, Calif., USA). Rabbit anti-human myelin basic protein (MBP) polyclonal antibody was used at 1:600 dilution (AB980; Chemicon international, Inc., Temecula, Calif., USA). Polyclonal anti-mouse MBP was used at 1:600 dilution (C-16; Santa Cruz biotechnology, Inc). Monoclonal mouse anti-human glial fibrillary acidic protein (GFAP) was used at 1:100 dilution (M0761; DakoCytomation Inc. Carpinteria, Calif., USA). Mouse monoclonal antibody [SM1-312] to Neurofilament (ab24574; Abcam) was used at 1:1000 dilution. Rabbit polyclonal anti-Olig 1 specific for oligodendrocytes (Ab5991; Chemicon) was used at 1:400 dilution. Positive and negative controls were included for each staining.

Luxol Fast Blue (LUB) staining was performed on paraffin embedded tissue of 7 micron in thickness mounted on a clean dry slide. Paraffin was removed and the sections were stained in solution A overnight at 57° C. (Solution A: 0.1% solution of Luxol fast blue (Solvent blue 38) by dissolving 1 gram of the substance in 1 liter of 95% ethanol together with 5 ml of 10% acetic acid). The section was immersed in 95% ethanol and excess stain washed off, followed by a wash in distilled water. This is followed by a 30 second immersion in 0.05% lithium carbonate, then several changes of 70% alcohol until gray and white matter can be distinguished. The section was washed in distilled water before staining with solution B for 5 minutes (Solution B:0.1% solution of Cresyl Violet Acetate in distilled water, before using, add 5 drops of 10% acetic acid to every 30 ml of solution and filter). The section was then washed in 95% ethanol followed by 2 washes in 100% ethanol, then 3 washes in xylene before it was mounted in permount (Fisher Scientific). Myelin fibers should be stained blue to greenish-blue and cells should be stained pink to violet.

Figure 7:
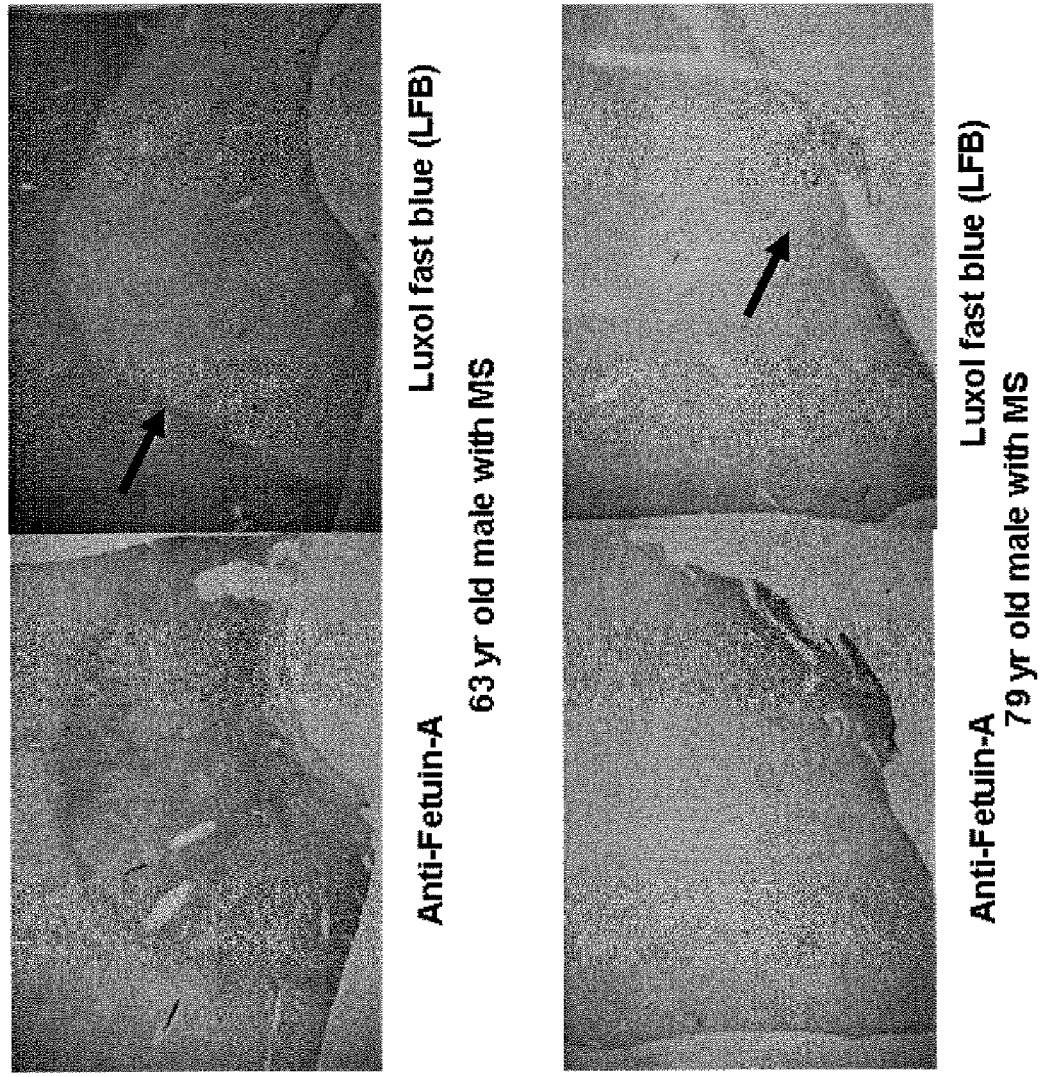
FIG. 7 is a microscopy image illustrating the increased levels of Fetuin-A in plaque areas of human MS brains detected by immunohistochemistry.

The presence of Fetuin-A protein was also compared by immunostaining in 10 normal and 22 MS human brain sections. For MS brains, the distribution of Fetuin-A protein was assessed in demyelinated plaques as well as in normal-appearing white and grey matter. Anti-fetuin-A immunostaining together with LFB staining in two MS brain sections from a 63 year old and a 79 year old man is shown in FIG. 7 in black and white. These images clearly show two plaques (areas where there is a loss of myelin) where there is elevated levels of Fetuin-A as indicated by the darker grey staining in the anti-Fetuin-A panels. The border between the regions of intact myelin and demyelination is indicated by an arrow, where the lighter grey staining in the LFB panels indicates areas of demyelination.

Figure 8A:
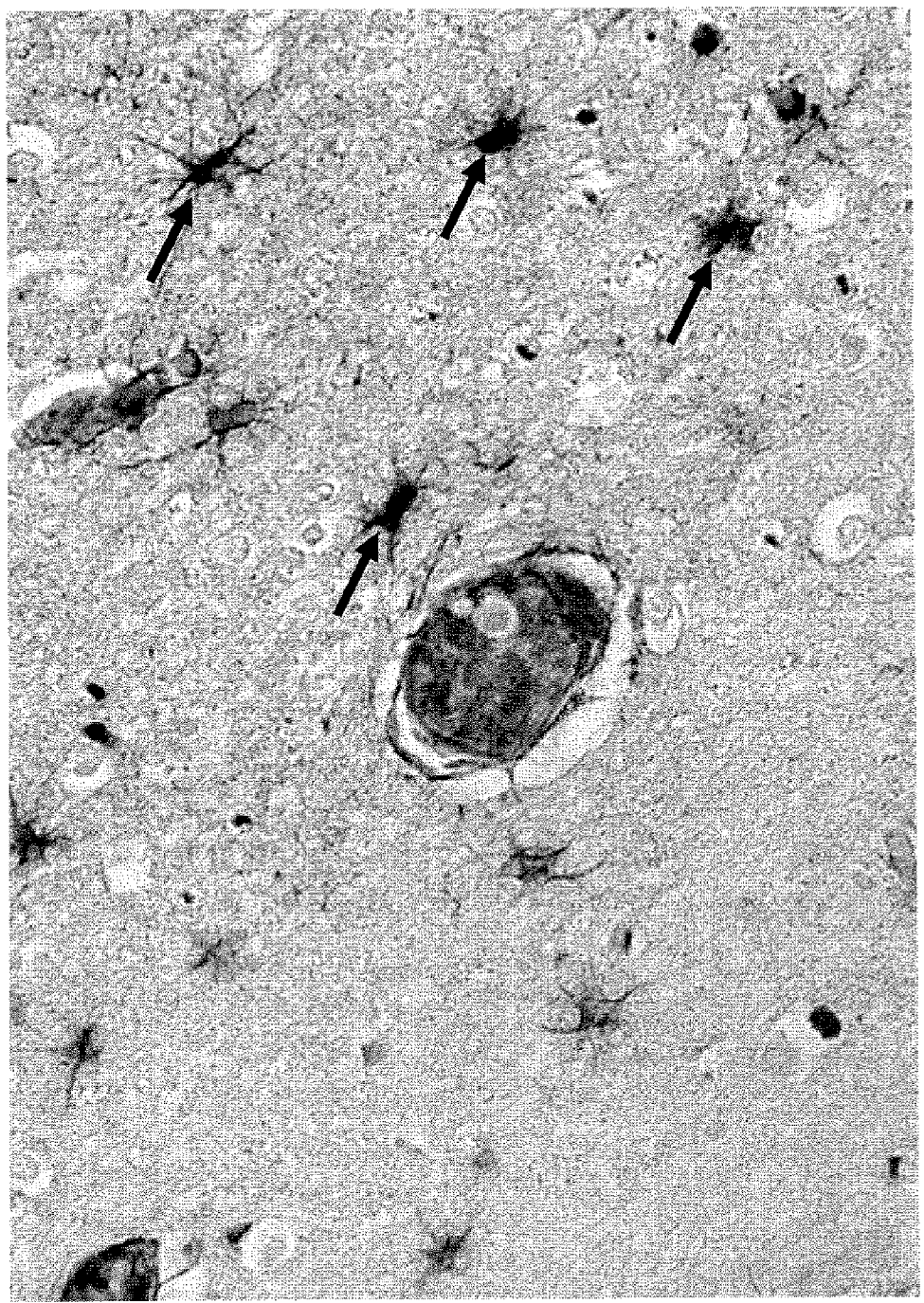
FIG. 8a is a microscopy image illustrating Fetuin-A protein in astrocytes detected by immunohistochemistry.
Figure 8B:
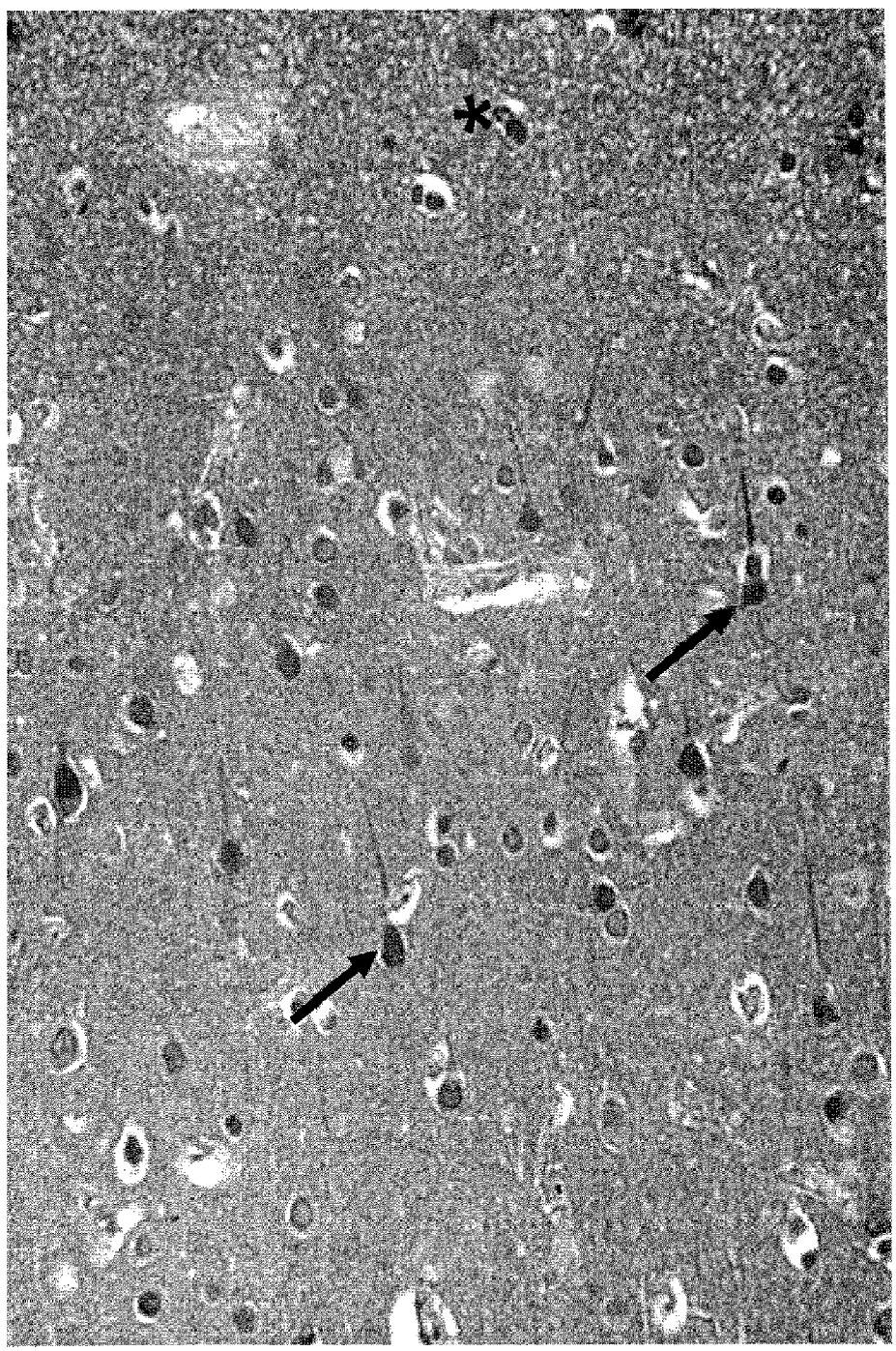
FIG. 8b is a microscopy image illustrating Fetuin-A protein in oligodendrocytes detected by immunohistochemistry.
Figure 8C:
FIG. 8c is a microscopy image illustrating Fetuin-A protein in neurons detected by immunohistochemistry.
Figure 8D:
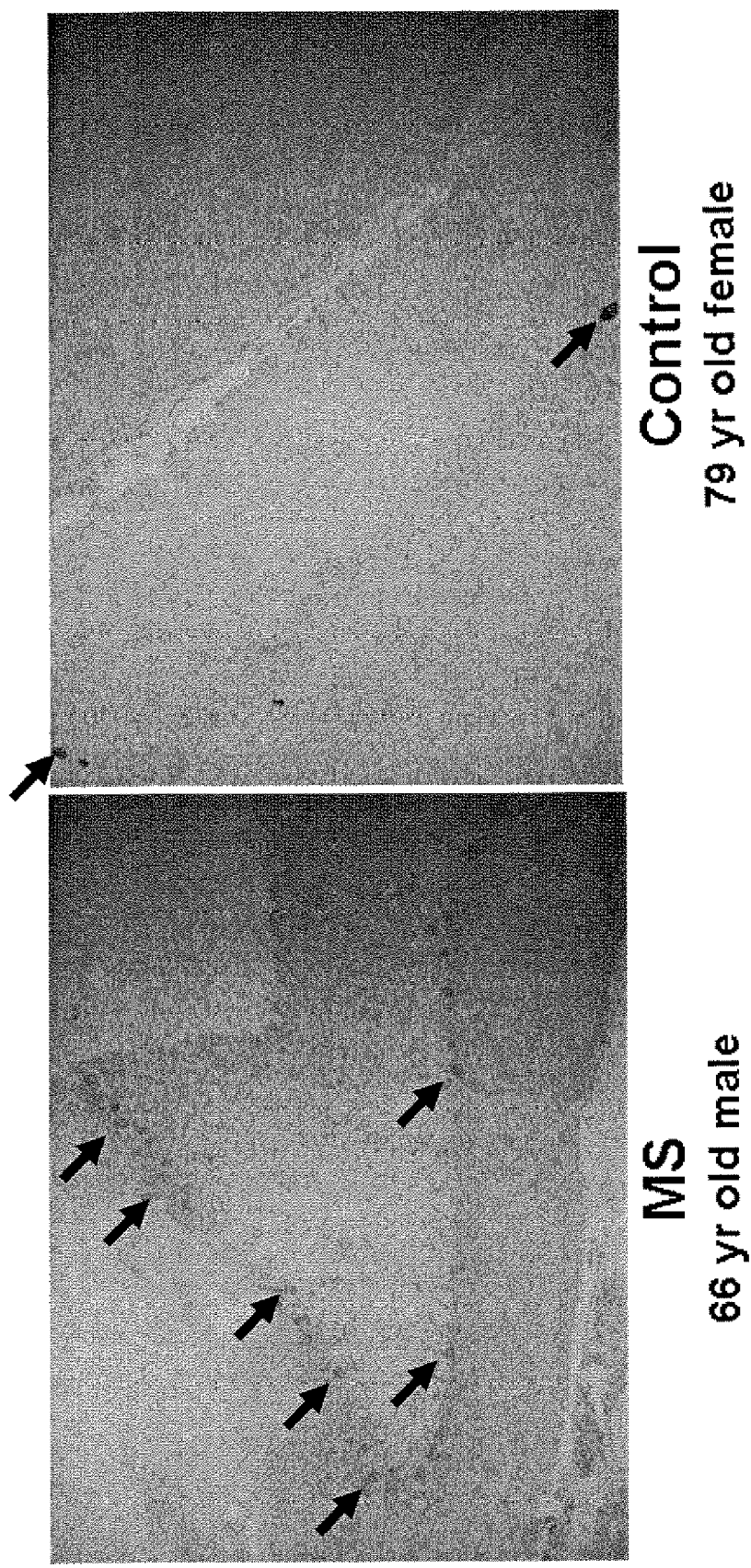
FIG. 8d is a microscopy image illustrating increased Fetuin-A positive Purkinje cells in the cerebellum of an MS patient detected by immunohistochemistry.
Figure 8E:
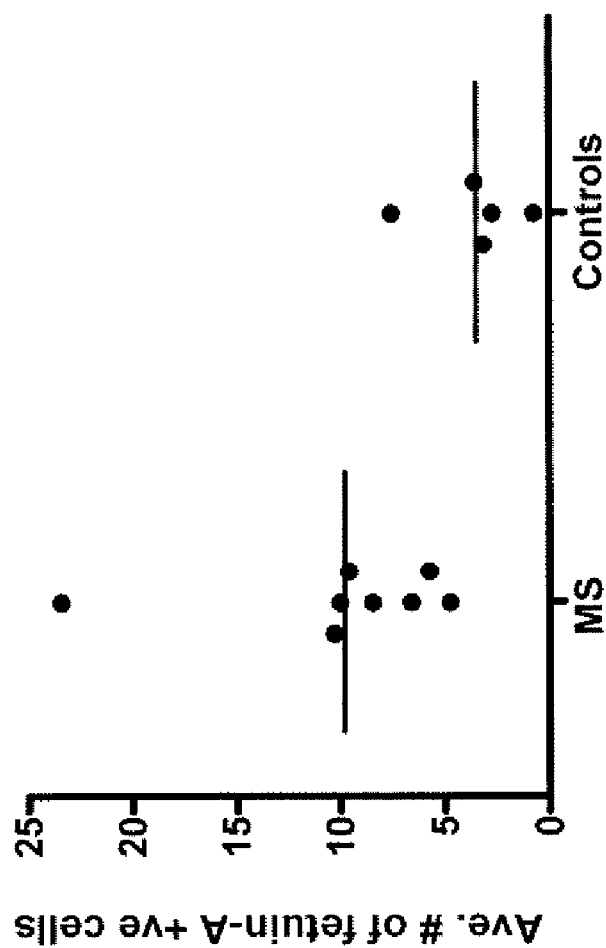
FIG. 8e graphically illustrates the quantification of Fetuin-A positive cells in the cerebellum of MS and control brains.

Fetuin-A was detected in many cell types of the CNS including astrocytes (FIG. 8a) indicated by the arrows and oligodendrocytes indicated by the asterisk (FIG. 8b). Fetuin-A protein was also detected in neurons indicated by the arrows in FIGS. 8b and 8c. In non-plaque areas, the most notable immunostaining for Fetuin-A was seen in the Purkinje cells (indicated by the arrows) of the cerebellum in MS brains, while in the cerebellum of normal brains very few positive cells were found (FIG. 8d). This finding was confirmed by counting Fetuin-A positive Purkinje cells from 7 random fields at ×10 magnification from the cerebellum of 5 control and 7 MS brains (FIG. 8e). The average numbers of fetuin-A positive cells in the MS brains was significantly higher than in the controls (P=0.01).

The antibody specific for Fetuin-A was used in these immunohistochemical stainings to look for the presence and localization of Fetuin-A in the brain. LFB (Luxol fast blue) stains normal myelin blue (dark grey in black and white figures) therefore where there is demyelination (loss of myelin) there is little or no staining (light grey in black and white figures). The areas of demyelination overlap with the areas of high Fetuin-A staining (using the anti-Fetuin-A antibody) as indicated by the brown DAB staining (dark grey in the black and white figures). Demyelination is an indication of disease activity and once again high levels of Fetuin-A are found here.

Quantitative PCR

The presence of Fetuin-A protein in the brain was visualized by immunohistochemistry, however in order to quantify the amount of Fetuin-A actually synthesized in the brain quantitative PCR (polymerase chain reaction) was performed. This technique allows for the actual quantification of the number of mRNA transcripts that are specific for Fetuin-A. RNA was extracted from 10 μm frozen sections of a total of 10 plaque regions from 8 different MS brains. RNA derived from control brain samples from 10 healthy donors was purchased from Stratagene (La Jolla, Calif.) and Chemicon (Temecula, Calif.) and included regions of the cerebellum, occipital, parietal, frontal, and temporal lobes. RNA was reverse transcribed into cDNA with random hexamers using the superscript RT kit (Invitrogen Cat. # 18080-051). Primers specific for the human Alpha$_2$ HS-glycoprotein gene (Accession # P67013) were designed and used to amplify a 155 bp region. The forward primer specific for the human Alpha$_2$ HS-glycoprotein gene (Ace No.: D67013) is: hAHSG-F: 5'-CTCAGCCGAGGACGT GCGCAAGG-3, (SEQ ID NO: 2) and the reverse primer is hAHSG-R: 5'-TGAGCCCGG-GAAATMTCCTCC-3' (SEQ ID NO: 3). The SYBR Green I kit from Roche (Cat. # 03515869001) was used with the Light Cycler 2.0. The cycle conditions were 95° C.-10 mins followed by 95° C.-10 sec, 65° C.-10 sec, 72° C.-15 secs for 40 cycles. The expression of Fetuin-A was compared to a house keeping gene (GAPDH) giving a normalized ratio. The expression of Fetuin-A was compared to a house keeping gene, Glyceraldehyde 3-phosphate dehydrogenase (GAPDH) giving a normalized ratio. The forward primer specific for the human GAPDH is 5'-ATCCCATCAC-CATCTTCCAG-3' (SEQ ID NO: 4) and the reverse primer is 5'-TGACTCCTTCCACGATACCA-3' (SEQ ID NO: 5).

Figure 9:
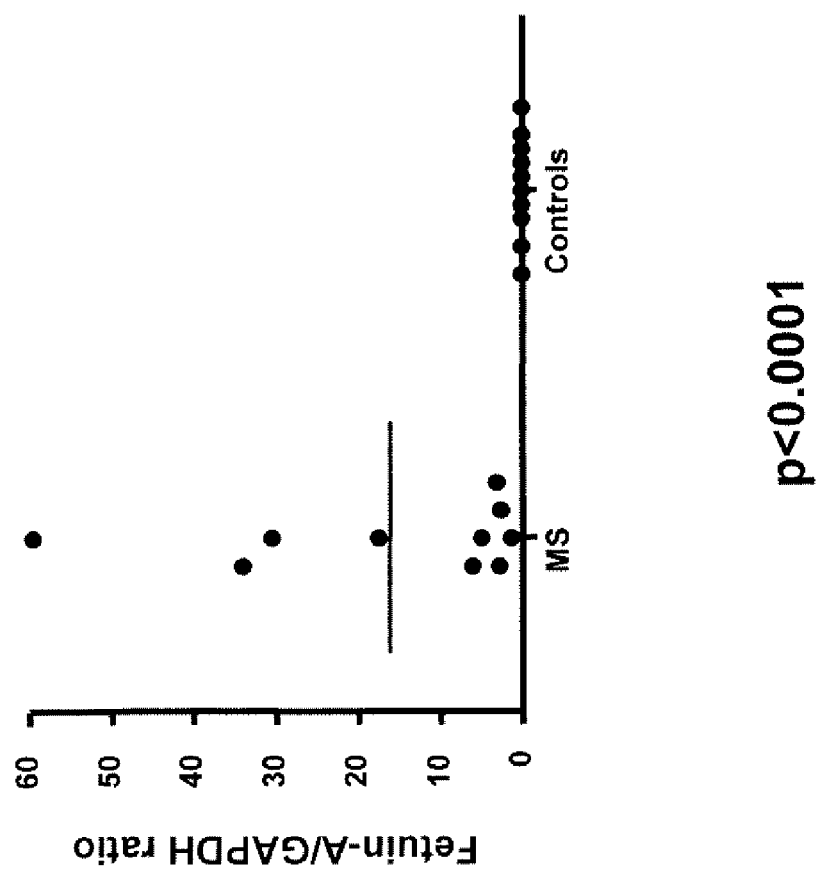
FIG. 9 graphically illustrates increased Fetuin-A expression detected by quantitative PCR in MS brains compared with healthy controls.

Results from quantitative PCR illustrated in FIG. 9 showed that Fetuin-A expression levels were significantly higher (approx. 40,000 fold) in MS than in normal brains [p<0.0001]. The average fetuin-A/GAPDH ratio in MS brains was 16.2 compared to only 0.0004 in control brains. This confirmed the immunohistochemistry findings and also showed that the level of Fetuin-A messenger RNA (mRNA), not only the protein level, is elevated in the CNS of MS patients.

Experimental Autoimmune Encephalomyelitis (EAE)

Experimental Autoimmune Encephalomyelitis (EAE), also called Experimental Allergic Encephalomyelitis, is an animal model of Multiple Sclerosis. Animal models of human diseases are diseases of non-human species (often rodents) which closely resemble their human counterparts and can be studied with a view to better understanding and treating the human form. EAE is not multiple sclerosis, nor is it a single disease in a single species, but its different forms resemble the various forms and stages of MS very closely in a large number of ways.

EAE is an acute or chronic-relapsing, acquired, inflammatory and deymyelinating autoimmune disease of the CNS. The animals are injected with the whole or parts of various proteins that make up myelin, the insulating sheath that surrounds nerve cells (neurons). These proteins induce an autoimmune response in the animals—that is the animal's immune system mounts an attack on its own myelin as a result of exposure to the injection. The animals develop a disease that shows pathological and clinical similarities to MS in humans.

EAE has been induced in a number of different animal species including mice, rats, guinea pigs, rabbits, macaques, rhesus monkeys and marmosets. For various reasons including the number of immunological tools, the availability, lifespan and fecundity of the animals and the resemblance of the induced disease to MS, mice and rats are the most commonly used species.

The animals are in-bred to reliably produce susceptibility to EAE in the animals. As with humans and MS, not all mice or rats will have a natural propensity to acquire EAE. Moreover, different breeds will develop different forms of EAE, some of which act as good models for the different human forms of MS. Different EAE forms are also used as models for the different stages of MS.

Induction and clinical evaluation of EAE. The protocol for induction of EAE in mice was followed as described in Stromnes, I. M. and Goverman, J. M., Active induction of experimental allergic encephalomyelitis. *Nat Protoc* 1 (4), 1810 (2006). C57BL/6 Mice were inoculated with myelin oligodendrocyte glycoprotein (MOG) peptide fragment 35-55 (MEVCWYRPPFSRVVHLYRNGK) (SEQ ID NO: 4) emulsified in complete Freund's adjuvant (CFA) by injecting 0.2 ml of emulsion made by mixing equal volumes of 1 mg/ml MOG in PBS (phosphate buffer solution) and 4 mg/ml mycobacterium tuberculosis H37Ra (Difco Laboratories, Detroit, Mich.). Twenty-four hours later each mouse received by i.p. injection 300 ng pertussis toxin (List Biological Laboratories, Inc., Campbell, Calif., USA). Clinical severe score was assessed on a 0 to 5 scale as follows: grade 0, normal; grade 1, tail paralysis; grade 2, tail paralysis and hind-limb weakness (waddling gait); grade 3, hind limb paralysis; grade 4, hind limb plus forelimb paralysis; grade 5, moribund state. An amelioration was defined as a sustained decrease (more than 2 days) in at least one full grade in clinical score after the animal had progressed previously at least a full clinical score and had stabilized for at least 2 days. The data are plotted as mean clinical score for all animals in a particular therapeutic group.

Figure 10:
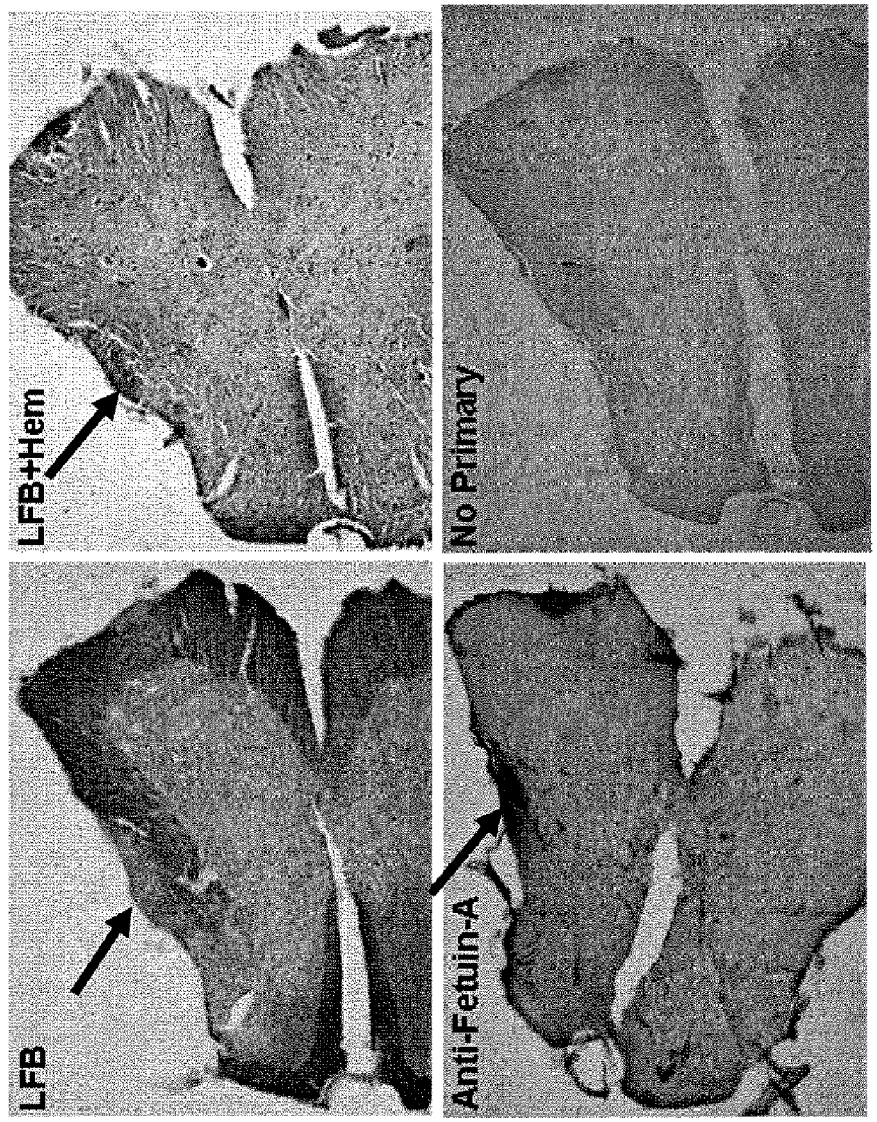
FIG. 10 illustrates increased Fetuin-A expression in active experimental autoimmune encephalomyelitis (EAE) plaques detected by immunohistochemistry.

Spinal cords of C57BL/6 mice were obtained at day 28 after EAE induction at the peak of disease when the EAE score was between 3 and 4. Immunohistochemical analysis illustrated in FIG. 10 in black and white revealed regions of demyelination where there is little or no LFB staining (areas of light grey staining indicated by the arrow in the LFB panel) has significantly higher levels of Fetuin-A protein (darker grey staining indicated by the arrow in the anit-Fetuin-A panel) compared to other spinal cord regions where myelin is intact. Also the demyelinated regions are also areas where there is active inflammation (indicated by the arrow in the LFB+Hem panel) where there are infiltrating cells.

Treatment with Anti-fetuin-A and fetuin-A. The mice were divided into treatment groups: (1) Control PBS; (2) anti-fetuin-A (Monoclonal anti-mouse fetuin-A 0.5 mg/ml (R&D systems, Minneapolis, Minn., USA), 20 ug/mouse; and (3) Bovine fetuin-A (Sigma), 1 mg/mouse. Each treatment group consisted of 4 mice and anti-fetuin-A, fetuin-A or PBS alone were injected every other day intraperitoneally (i.p.) from the day 16 (DAY 0) after EAE induction for a total of 5 times (at DAY 0, 2, 4, 6 and 8). The mice were monitored and scored for EAE on a daily basis.

Figure 11:
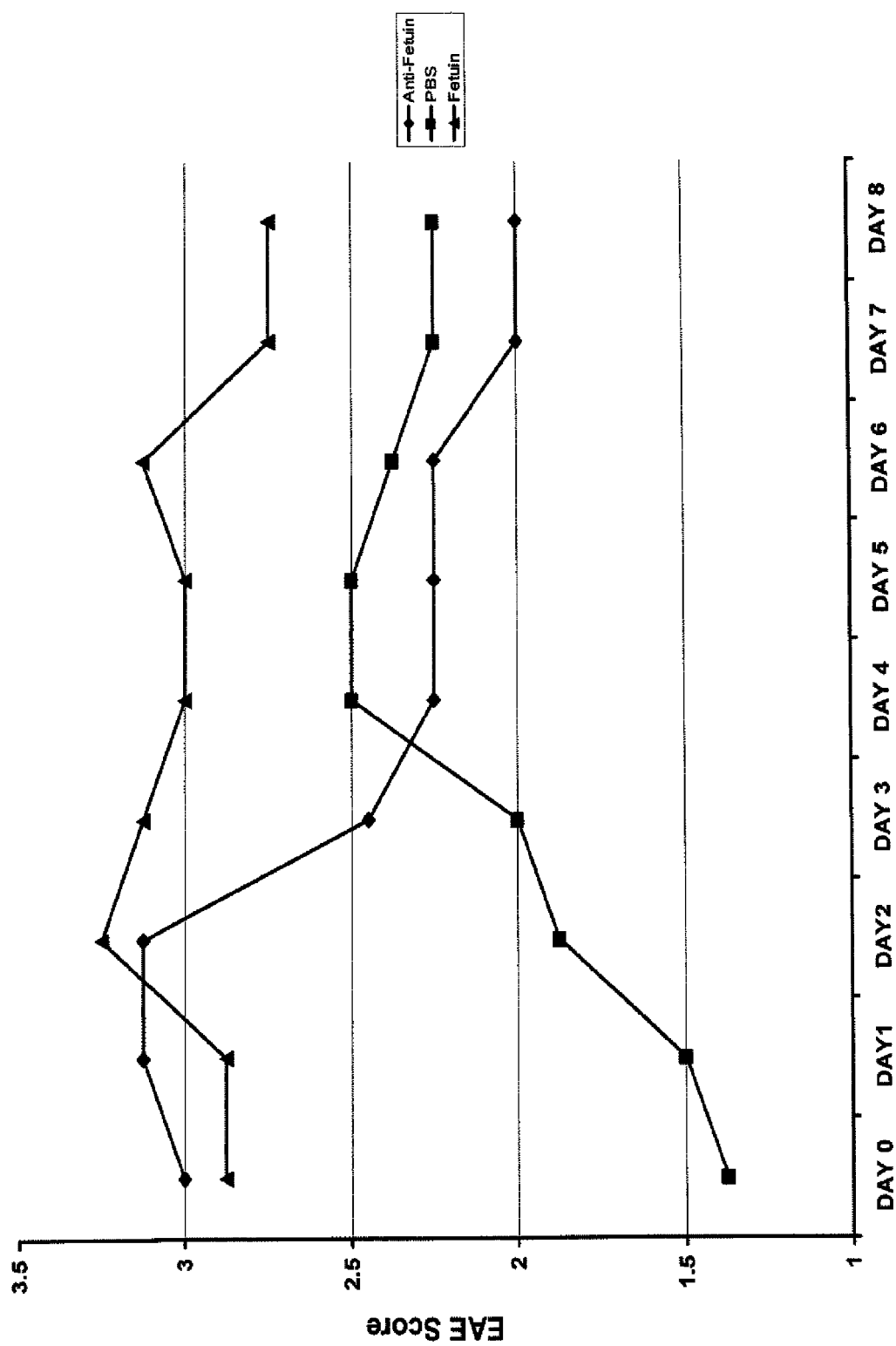
FIG. 11 graphically illustrates the EAE scores over time following treatment of mice with Fetuin-A and anti-Fetuin-A.

Results showed that treatment with anti-fetuin-A antibody resulted in an amelioration of EAE while mice administered with Fetuin-A protein seemed to have worsened disease when compared to the PBS control group (FIG. 11). After the fifth and final administration of fetuin-A or anti-fetuin-A antibody, the mice in all treatment groups gradually got worse EAE and by day 20 they all had an average LAE score of 3.

Using Fetuin-A as an Indicator of Treatment Response to Tysabri®

Tysabri® (Biogen Idec, Boston, Mass., or nataluzimab, is a humanized monoclonal antibody that binds to the α4-integrins on the surface of leukocytes (white blood cells). Binding of the antibody blocks the interaction of α4-integrins with vascular cell adhesion molecule 1 (VCAM-1) on endothelial cells and thereby prevents migration of white blood cells across the blood brain barrier. The ability of Tysabri® to suppress leukocyte entry into the CNS is believed to mediate its therapeutic effects for MS. Since Fetuin-A is a marker for disease activity in MS we decided to test its utility as an indicator of treatment response to Tysabri®. CSF samples were obtained pre-treatment and 6 months post-treatment. In addition MRI exams were done within 2 weeks of obtaining the CSF. The level of Fetuin-A in the C(SF was measured by ELISA and the disease activity at the time of CSF sampling was assessed by using the same criteria as previously described: (1) one or more relapses in the past 6 months; (2) change of one point or greater in EDSS (Expanded Disability Status Scale) score in the past 6 months; and (3) change in MRI, specifically a change in the number and/or size of lesions and the presence of gadoliniuim enhancing lesions in the past 6 months.

Figure 12:
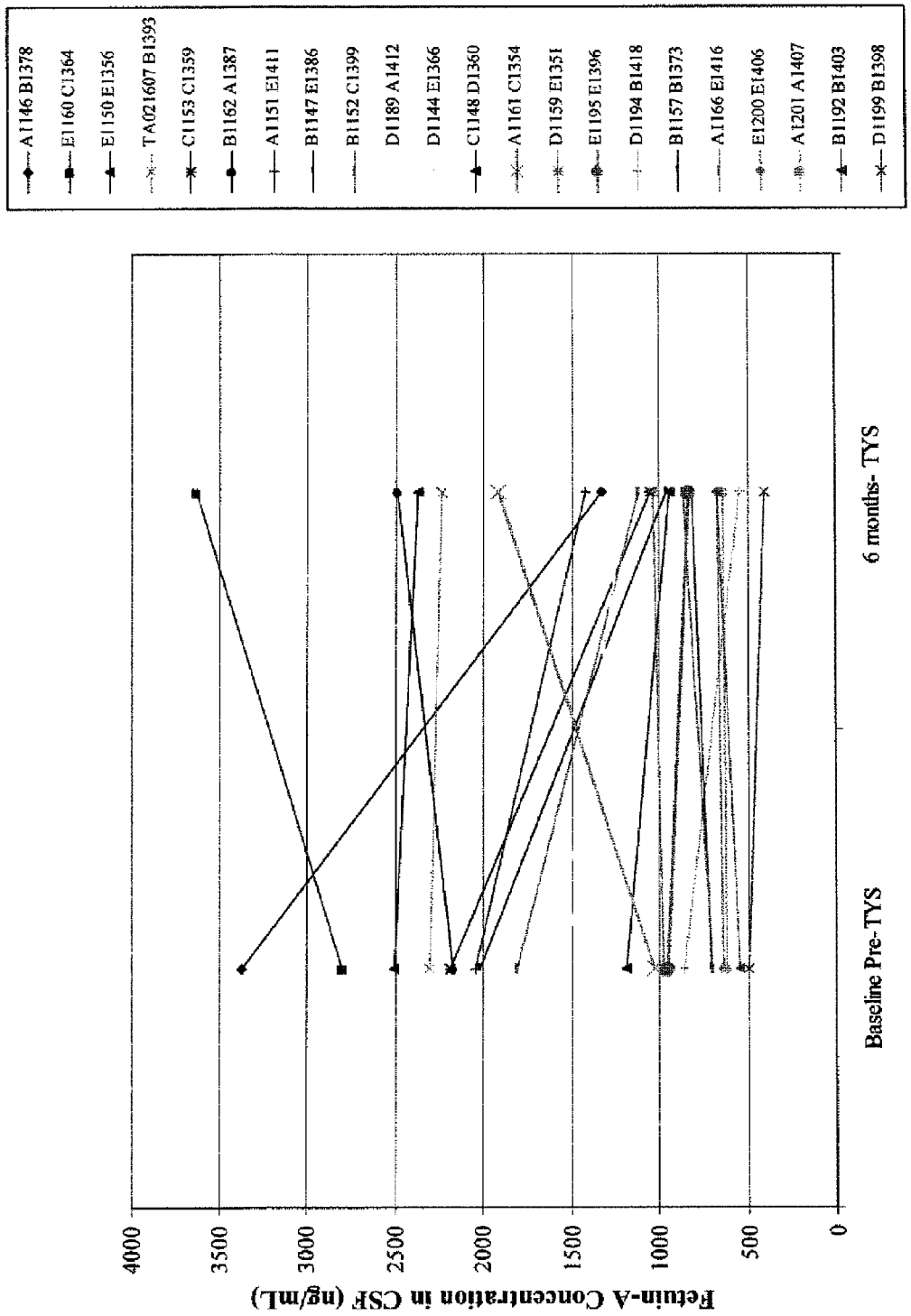
FIG. 12 graphically illustrates the levels of Fetulin-A in CSF measured by ELISA pre- and post-Tysabri® treatment.

The average Fetuin-A concentration before Tysabri treatment was higher than post-treatment, 1538 ng/mL vs 1309 ng/mL. This reflects the general trend of decreasing Fetuin-A levels as Tysabri® treatment progressed and lead to decreased disease activity. However there were certain patients whose Fetuin-A levels increased after 6 months of treatment and had worsening disease. These non-responders were taken off Tysabri® as a result. FIG. 12 shows the levels of Fetuin-A measured pre- and post-treatment in 21 patients. As expected due to the heterogeneous nature of MS there is always significant variability in response to therapeutic agents. These results provide an indication of the potential utility of measuring Fetuin-A protein levels in the CSF as a gauge for determining treatment response in MS.

It is believed that Fetuin-A could also be used as a marker for testing disease activity in conjunction with other MS therapeutic agents such as Copaxone® (glatiramer acetate), Avonex® (interferon beta-1a) and Rebif® (interferon beta-1a).

The disclosures of publications within this application are hereby incorporated by reference in their entireties to more fully describe the state of the art to which this invention pertains. The discussion of the references herein is intended merely to summarize the assertions made by the authors and no admission is made that any reference constitutes prior art. Applicants reserve the right to challenge the accuracy and pertinence of the cited references The foregoing is illustrative of particular embodiments and features of the present invention. In view of the teaching presented herein, one of skill in the art could readily select other materials for use in the formulation. The foregoing disclosure is not limiting upon the present invention but is illustrative of the principles thereof. All equivalent relationships to those illustrated in the drawings and described in the specification are intended to be encompassed by the present invention. It is the following claims, including all equivalents, which define the scope of the invention.

What is claimed is:

1. A method for monitoring the efficacy of a therapeutic agent used for treating multiple sclerosis, the method comprising measuring the level of fetuin-A protein pre and post treatment, wherein a decrease in the level of said fetuin-A protein indicates efficacy of said agent.

2. The method of claim 1, wherein the therapeutic agent is nataluzimab.

3. The method of claim 1, wherein the fetuin-A protein is represented by the amino acid sequence in SEQ ID NO: 1.

* * * * *